(12) United States Patent
Samson et al.

(10) Patent No.: US 6,186,978 B1
(45) Date of Patent: *Feb. 13, 2001

(54) BRAID REINFORCED INFUSION CATHETER WITH INFLATABLE MEMBRANE

(75) Inventors: Gene Samson, Milpitas; Hong Doan, Santa Clara; Kim Nguyen, San Jose, all of CA (US)

(73) Assignee: Target Therapeutics, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/903,719

(22) Filed: Jul. 31, 1997

Related U.S. Application Data (63) Continuation-in-part of application No. 08/729,241, filed on Oct. 9, 1996, which is a continuation of application No. 08/689,464, filed on Aug. 7, 1996, now abandoned.

(51) Int. Cl.[7] .................................................. A61M 29/00
(52) U.S. Cl. ...................... 604/96.01; 604/525; 604/527; 606/194; 606/195
(58) Field of Search ......................... 604/96, 282, 99.04, 604/101.01, 101.04, 527, 525, 96.01; 606/194–195

(56) References Cited

U.S. PATENT DOCUMENTS 5,176,661   1/1993   Evard et al. .
5,728,063   3/1998   Preissman et al. .
5,728,065   3/1998   Follmer et al. .

FOREIGN PATENT DOCUMENTS

0375775      7/1990   (EP) .
WO 96/15824  5/1996   (WO) .

*Primary Examiner*—Mark Bockelman
(74) *Attorney, Agent, or Firm*—Morrison & Foerster LLP (57) ABSTRACT

This is a surgical device particularly a perfusion catheter having an inflatable membrane or balloon located at the distal end of the catheter shaft. The catheter shaft is comprised of an outer tubing assembly and an inner tubing assembly separated by an open annulus for inflating and deflating the inflatable membrane. The assembly may additionally comprise an inflatable membrane which is detachable. The outer tubing assembly is made up of at least one polymeric layer and a braid which may be polymeric or metallic, perhaps of a super-elastic alloy. At least a portion of the inner tubing assembly is made up of at least one polymeric layer and preferably a super-elastic metallic braid. The inner tubing assembly includes a lumen through which a guidewire may pass. It is further desirable that the inner tubing assembly include a coil member which generally is coextensive with the balloon along its axis. That lumen is preferably lined with a lubricious polymer. The outer tubing assembly allows the profile of the catheter to be minimized and yet provides significant kink-resistance to the inner tubing assembly. The structure of the inner tubing assembly provides resistance to premature inflation during introduction of infusate through the inner lumen.

18 Claims, 11 Drawing Sheets

BRAID REINFORCED INFUSION CATHETER WITH INFLATABLE MEMBRANE

RELATED PATENT APPLICATIONS

This application is a continuation-in-part of U.S. patent application Ser. No. 08/729,241 filed Oct. 9, 1996 pending which is continuation of Ser. No. 08/689,464 filed Aug. 7, 1996, now abandoned.

FIELD OF THE INVENTION

This invention is a surgical device. In particular, the invention is a perfusion catheter having an inflatable membrane or balloon located at the distal end of the catheter shaft. The catheter shaft is comprised of an outer tubing assembly and an inner tubing assembly separated by an open annulus for inflating and deflating the inflatable membrane. The assembly may additionally comprise an inflatable membrane which is detachable. The outer tubing assembly is made up of at least one polymeric layer and a braid which may be polymeric or metallic, perhaps of a super-elastic alloy. At least a portion of the inner tubing assembly is made up of at least one polymeric layer and preferably a super-elastic metallic braid. The inner tubing assembly includes a lumen through which a guidewire may pass. It is further desirable that the inner tubing assembly include a coil member which generally is coextensive with the balloon along its axis. That lumen is preferably lined with a lubricious polymer. The outer tubing assembly allows the profile of the catheter to be minimized and yet provides significant kink-resistance to the inner tubing assembly. The structure of the inner tubing assembly provides resistance to premature inflation during introduction of infusate through the inner lumen.

BACKGROUND OF THE INVENTION

This invention relates generally to a catheter having an expandable membrane or balloon at its distal tip. It is constructed so that it has two lumens; one is central lumen for a guidewire or for the introduction of drugs or vaso-occlusive materials or devices, and the other is coaxial about the interior lumen and is used solely for the purpose of inflating or deflating the distal inflatable membrane. The device is designed is such a way that it has a very narrow overall diameter and it is preferably constructed using a compliant balloon as the membrane. This is to say that the balloon section located distally on the inventive catheter is of the same general diameter as is the catheter shaft in the near neighborhood of the inflatable membrane, and yet will expand to as much as four or five times the diameter of the device when so inflated. Because of the very narrow configuration of the device, it may be used in regions of the body where prior balloon catheters are not suitable. This is to say that it may be used in the vasculature of the brain and the periphery as well as in the soft organs, such as the liver. It is of significantly small enough diameter that it may be used in various genito-urinary passageways without undue hardship on the patient. Also central to the invention is the use of a braid in the outside tubing assembly, desirably either metallic or of polymeric filaments. At least a portion of the inner tubing assembly of the inventive catheter, generally the more proximal portion, comprises a metallic braid, often a metallic or super-elastic alloy ribbon braid. This super-elastic alloy braid provides exceptional kink resistance, not just to the tubing assembly in which it is placed, but more surprisingly to the inner tubing assembly. The inner braid prevents the balloon from expanding during introduction of fluids through the inner lumen or the inner lumen from collapsing when the balloon is inflated. The inner tubing asembly also preferably comprises a coil section in the region of the inflatable membrane to provide enhanced flexibility.

Catheters having a coaxial structure are known. Many of them are used in procedures such as percutaneous transluminal angioplasty (PTA). In such procedures, however, the balloon is a noncompliant one. That is to say, it is of a specific size which is set upon the time of its manufacture. The balloon itself is folded or collapsed into a somewhat bulky and stiff region which is difficult to maneuver, both through the guiding catheter by which it is placed and through the various vascular lumen to the site of treatment. In such a procedure, a guiding catheter typically having a pre-shaped distal tip, is introduced into the vasculature of the patient. The catheter is then advanced from the entry site in the femoral artery up into the aorta. Once the tip of the catheter reaches the aorta, the distal end of the catheter is twisted or "torqued" so to turn the preshaped distal tip of that guiding catheter into the ostium of the desired coronary artery. A balloon-bearing catheter is then advanced through the guiding catheter and out its distal tip until the dilatation catheter's balloon extends across the region to be treated. The balloon is then expanded to the predetermined size, often by the use of a radio-opaque liquid at relatively high pressures. Upon completion of the procedure, the balloon is then deflated so that the dilatation catheter may be removed and thereafter the blood flow is restored through the thus-treated artery.

In other procedures, a balloon-bearing catheter, typically of a somewhat smaller diameter than a catheter used in PTA procedures might be used. In a universal sense, the procedure might be considered to be similar, since a guiding catheter is initially placed so that its distal end is near the site to be treated or diagnosed. The balloon catheter would then be placed through the lumen of the guiding catheter to that site. The balloon-bearing catheter, perhaps with a guidewire extending through an existing central lumen, could then be extended from the distal side of the guiding catheter to the treatment or diagnostic site. The balloon would then be expanded, and once the procedure is complete, the balloon deflated and removed from the body. In some instances, the balloon might be of a compliant nature rather than of a fixed diameter configuration found in a typical PTA balloon.

The advent of interventional radiology and its sub-practice, interventional neuroradiology, as a viable treatment alternatives in various regions of the body having tortuous vasculature often surrounded by soft organs, has produced demands on catheterization equipment not placed on devices used in PTA. The need for significantly smaller diameter devices and particularly those which have variable flexibility and are able to resist kinking is significant.

U.S. Pat. No. 5,338,295, to Cornelius, et al., describes a dilatation balloon catheter having a shaft formed of a tubular braid of a stainless steel material. The proximal outer tube section is encased in a polyimide material. The distal outer tube section which forms a balloon is made of a polymeric material such as polyethylene.

Another similar device is shown in U.S. Pat. No. 5,451, 209, to Ainsworth, et al. Ainsworth, et al., describes a composite tubular element useful in intravascular catheters. In particular, it is said to be useful as an element of a fixed wire dilatation catheter or in a guiding or angiographic catheter. The structure of the device is formed by braiding strands which are formed from a mixture of a polymeric matrix material (e.g., a fiber or powder) having a relatively low melting point in a high strength reinforcing fiber having a relatively high melting point. The fibers are woven into a tubular element, the resulting braided tubular element is heated to melt the matrix material so to permit it to flow around the high melting point reinforcing fibers. This procedure forms a matrix. Thermoplastic jackets or coatings are then extruded onto or otherwise applied to the exterior of the thus-produced braided tubular element.

U.S. Pat. No. 5,429,597, to DeMello, teaches a balloon catheter which is said to be kink resistant. In general, it appears to be made up of an outer polymeric covering over a "cross-wound multifilar (CWMF) coil in a nonfixed removable core wire." The CWMF coil is a pair of helical coils which are wound in opposite directions so to provide torque transmission during use of the catheter. There appears to be no suggestion of weaving the CWMF materials into a braid.

PCT application to Pray, et al. (WO93-20881) assigned to SciMed Medical Systems suggests a dilatation catheter having a shaft with a proximal section which is a composite of polymeric materials and a stainless steel braid tube. The distal section of the catheter is formed of a flexible polymeric tube. In one embodiment of the described device, the braid weave of the proximal section of the shaft has a varying pick count, increasing in the distal direction. This provides for increased distal flexibility.

Published U.K. Patent Application GB-2,233,562A by Hannam, et al., shows a balloon catheter having a flexible, hollow inner shaft and an outer braided shaft with a balloon. The balloon is inflated by the use of fluid introduced between the inner and outer shafts. The inner shaft is fixed relative to the outer shaft at both ends, so that when the balloon is inflated, the outer shaft shortens. The excess length of the inner shaft is accommodated by the process of that inner shaft bending into a coil-like form within the outer shaft lumen. The braid is said typically to be of a fabric of a polyester floss. It is said to extend the entire length of the outer shaft but may include a varying pick rate apparently in the neighborhood of the balloon. The balloon is made of the same material as the braided layer, and has a flexible elastic polyurethane covering.

U.S. Pat. Nos. 5,032,113 and 5,476,477 to Burns, show a partially coaxial catheter having a region of the device which is coaxial in nature. The innermost lumen is used for passage of a guidewire. The outer annular lumen is used to inflate a balloon with which it is in hydraulic communication. The outer annular lumen is also in hydraulic communication with the inner lumen. A variety of flow reducing means are shown as being in mid-catheter to permit the passage of fluids at some controlled rate in and out of the balloon.

U.S. Pat. No. 5,460,607 shows another coaxial catheter in which the conventional balloon is open to an annular space between an inner and an outer tubing. One variation of the disclosed device is said (at column 12) to include a balloon made of a material such as polyurethane. In that variation, the inner tube (130) is said to be made of a hard tube, a metal spring reinforced tube, a fine stainless steel tube, etc.

U.S. Pat. No. 5,460,608 to Lodin, et al., shows a balloon catheter having an outer tubing shaft and an inner tubing shaft in which the inner shaft is constructed in such a way so as to "prevent it from collapsing or breaking" during use. It is said to be a dilatation catheter used in PTA in large peripheral vessels. The inner tubing is strengthened by the use of a reinforcing coil. The balloon is further said to be made preferably of polyethylene terephthalate.

U.S. Pat. No. 5,470,313, to Crocker et al, shows another variation of a balloon catheter with an inner and outer tubing assembly partially separated so to form a region between the two assemblies. The balloons described in conjunction with this device are not generally compliant, but are designed in such a way that they have variable diameters when inflated. This is done by the placement of bands at various sites around the circumference of the balloon.

U.S. Pat. No. 5,480,383, to Bagaoisan et al, is to a balloon catheter having an inner and outer tubular member with proximal portion of the inner tubular member being formed of a pseudoelastic alloy. The section appears to be tubular.

U.S. Pat. No. 5,480,380, to Martin, shows a dual lumen catheter in which the inner and outer lumens are equipped with orifices to allow materials placed within the catheters to perfuse into a selected treatment area.

None of the devices in the documents discussed above describe a catheter having the structure specified herein.

SUMMARY OF THE INVENTION

This invention is a catheter used for insertion into some lumen of the human body. In general, it is to be used in a vascular lumen in which high flexibility without the aspect of kinking is a desirable trait. Such vascular lumens would normally be found in the brain, the liver, and in certain peripheral areas of the body. The inventive catheter is nonetheless suitable for treatment of other body lumen, such as may be found in the genito-urinary system.

The physical structure of the inventive catheter includes an inner and an outer tubing assembly separated by an annular space. At the distal end of the outer tubular member may be found an expandable membrane typically in the form of a plastic or compliant balloon. Desirably, the diameter of the uninflated balloon is the same as that of the exterior of the catheter shaft just proximal of the balloon area. The inner tubing assembly is open from the proximal end through the distal end. The annular space between the two tubing assemblies is not in fluid communication with the inner lumen and is used solely for the purpose of inflating and deflating the inflatable distal membrane. Central to some variations of this invention is the use of a super-elastic, ribbon braid which is integrated in some fashion into at least a portion of both the inner and outer tubing assemblies. The outer tubing assembly having this ribbon braid acts as a member which prevents kinking both of the inside assembly and the outside assembly of which it is a part.

Other highly desirable variations of the invention include those in which the outer tubing assembly utilizes a braided polymeric member in at least the distal portion of the member instead of the super-elastic alloy ribbon member.

The inner tubing assembly also desirably includes a super-elastic, ribbon braid which is integrated into the polymeric tubing wall. This provides protection against kinking and inappropriate inflation of the balloon during the time other procedures are taking place.

In one variation of the invention, the braid in the outer tubing member extends to a point just proximal of the interior of the inflatable membrane. The braid in the inner tubing assembly then provides for overall stiffness of the catheter assembly particularly in the distal region.

The braid in the outer tubing assembly itself may also be used as a stiffener in the overall catheter assembly by extending the braid through the inner space of the expandable membrane. In this variation, the inflation fluid will pass through the interstices of the braid structure from the annular space between the tubing assemblies into the balloon itself. In still another desirable variation, the inner tubing assembly utilizes a coil in the region of the inflatable membrane.

The catheter most desirably has an inner layer of a lubricious polymeric tubing situated as the innermost surface of the interior tubing assembly. This inner lubricious layer may extend all the way from the proximal end to the distal tip.

The balloon member used in this inventive catheter assembly may be either elastomeric and, hence, radially complaint to provide for a variety of functions not typically attempted by use of polyethylene or PET balloons. It may as well be a noncompliant balloon. If a noncompliant balloon is used, however, the catheter assembly loses some measure of its flexibility both literally and figuratively. Included in this invention is the presence of a detachable balloon placed on the distal end of the inner lumen.

It is highly desirable that the overall structure of the balloon be tailored in such a way that the most proximal portion of the balloon is stiffest, the midsection is more flexible, and the distal section is most flexible. More or fewer regions of intermediate flexibility may be used as desired.

Finally, it is highly desirable that a meltable and flowable polymer such as polyurethane is used to penetrate the various braiding and provide some measure of a bond to any inner layers of the outer tubing assembly. This provides for a very thin walled catheter assembly having walls which are both lubricious in their own right, but able to support bonding with much more lubricious polymers.

The concept of this inventive balloon catheter is the provision of a highly flexible, highly compliant balloon catheter which is amenable to use in very distal vasculature. It is designed in such a way that despite the fact that it has a high flexibility, it is also quite resistant to kinking, particularly in the region just proximal to the balloon.

DESCRIPTION OF THE INVENTION

Figure 1A:
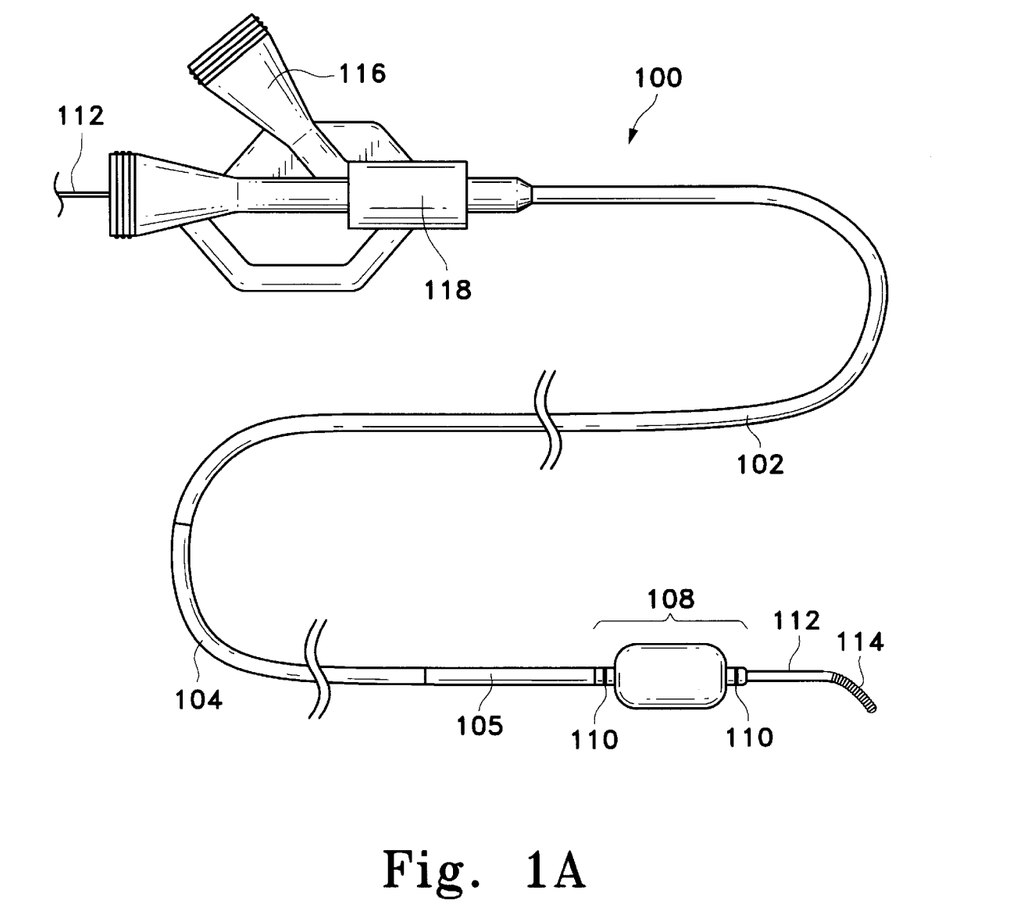
FIG. 1A shows a plan view of a typical catheter made according to the invention.

FIG. 1A shows a side view of a typical construction of a catheter assembly (100) made according to this invention. Catheter assembly (100) has, for purposes of illustration only, various regions which have different flexibilities. In the example shown in conjunction with FIG. 1A, the more distal section (106) of the catheter assembly (100) is more flexible than is the proximal section (102). A region of intermediate stiffness (104) is also depicted. The method of providing such stiffness and those lengths will be discussed in more detail below. However, it should be understood, that the invention is not limited to catheters having working shafts with specifically two or three regions of different flexibilities. That is to say that the complete length of working shaft of catheter assembly (100) may be of a single flexibility or may be of more than three distinct flexibilities or indeed the flexibility may vary in a wide variety of ways not specified herein. For instance, the catheter assembly (100) flexibility may vary as a function of the proximity to the distal end. When catheters such as these are used in soft organs, e.g., the liver or brain, it is more normal that the distal end of the catheter be more flexible. This flexibility may show up as a constantly variable value, although in certain instances it may be desirable to have a distal region of higher but specific flexibility.

Nevertheless, catheter assembly (100) is depicted with a catheter shaft of three discrete sections. The most proximal portion (102) is the stiffest in this variation. Middle shaft (104) of the catheter assembly (100) has a flexibility greater than that of proximal shaft (102), leaving the most distal portion (106) of catheter assembly (100) as the most flexible portion of the shaft proximal of the inflatable membrane (108). Radio-opaque markers (110) are shown on the proximal and distal portions of inflatable membrane section (108).

As will be discussed in more detail below, this catheter assembly (100) is one having an open lumen along its entire length so to allow guidewire (112) to pass through the proximal end of guidewire assembly (100) and extend out the distal end of catheter assembly (100). Included on the exemplified guidewire (112) is a radio-opaque coil (114). The structure of the guidewire forms no critical portion of this invention. Nevertheless, the catheter is of a design that will follow a guidewire into the tortuous vasculature of soft human organs such as the brain or the liver.

Figure 1B:
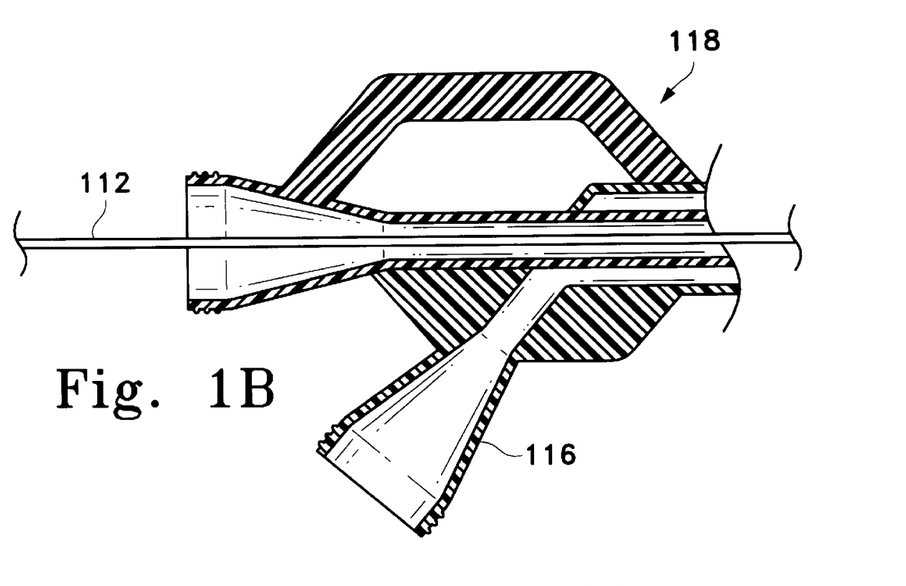
FIG. 1B shows a cutaway of the proximal end of the catheter assembly shown in FIG. 1A.

Also central to this invention, and discussed in more detail below, is the presence of an annular lumen which forms a closed system with balloon or membrane (108). The membrane is inflated and deflated through this annular lumen and is isolated from the central or guidewire-containing lumen. This annular lumen is fed with inflating fluid through a device such as a side arm (116) of luer (118). FIG. 1B shows the hydraulic communications of the luer assembly in greater detail. Side arm (116) and luer (118) have the usual threaded receptacles or fittings for attachment to, e.g., sources of inflation fluid, radio-opaque fluids for monitoring the passage of the catheter through the vasculature, saline solution for flushing the guidewire lumen, and others.

Figure 2A:
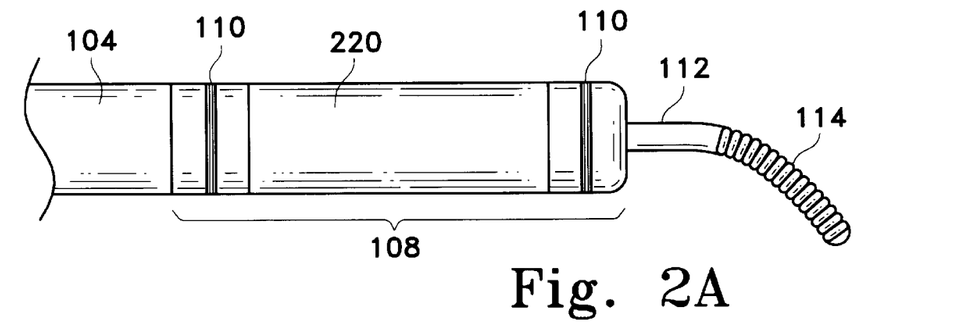
FIGS. 2A and 2B show a magnified plan view of the distal end of the catheter shown in FIG. 1A in which the inflatable membrane is not inflated (FIG. 2A) and is inflated (FIG. 2B).
Figure 2B:
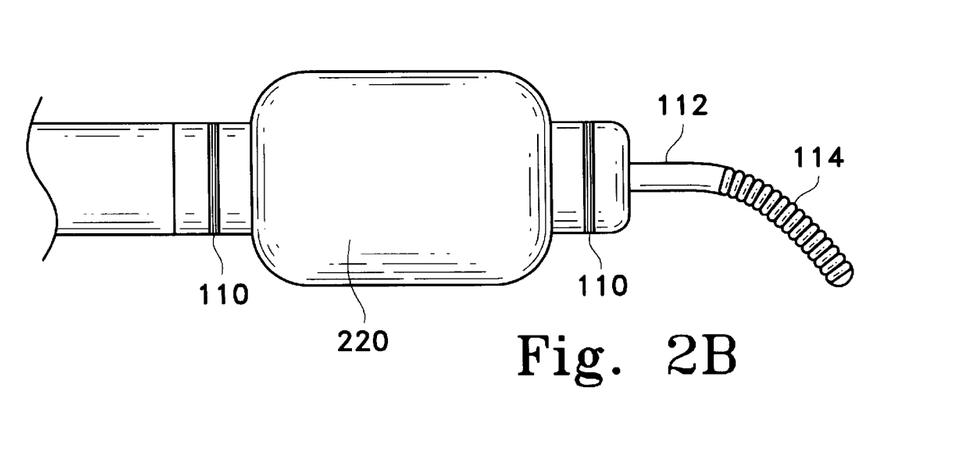

FIGS. 2A and 2B collectively depict one highly desirable aspect of this inventive catheter. Unlike the majority of other balloon catheters in existence and use today, this catheter desirably involves the use of a compliant inflatable membrane (220). The membrane (220) is of a compliant material and has elastomeric features. It is a balloon or membrane which will conform to the shape of the interior of a lumen within the vasculature. FIG. 2A shows a preferred variation of this invention in which the deflated membrane (220) is of the same general diameter as is the distal end of the midsection (104). This allows the catheter to be maneuvered in much more simple a fashion than catheters having inflatable, fixed-size balloons which are folded prior to introduction into the vasculature. The latter catheters often have balloons of, e.g., polyethylene, which are folded longitudinally during their traverse through the vasculature to reach their intended site. FIG. 2B shows membrane (220) in its inflated condition. Although the balloon is shown as having a flat aspect or constant diameter towards the midsection of its inflation profile, it may have other shapes, as well. Also shown in this pair of FIGS. 2A and 2B, are the distal and proximal radio-opaque bands (110) and guidewire (112) having radio-opaque (and likely shapable) coil (114) attached at its distal tip.

Figure 3:
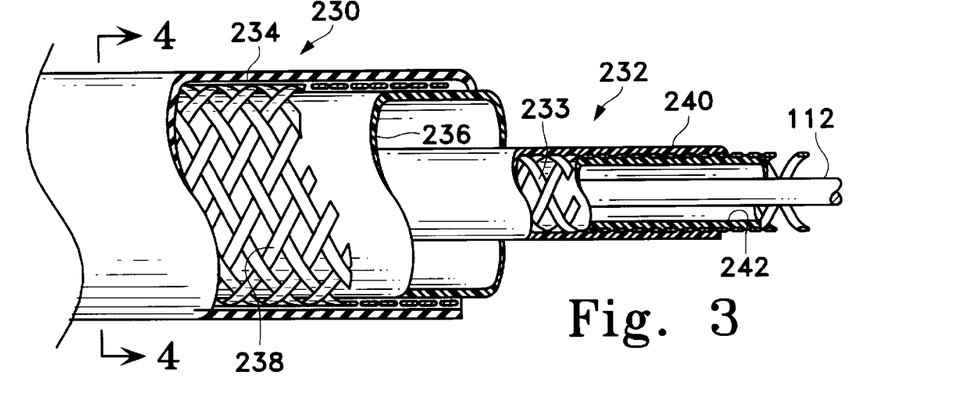
FIG. 3 shows partial cutaway of the inner and outer tubing assemblies forming at least one section of a catheter such as is shown in FIG. 1A.
Figure 4:
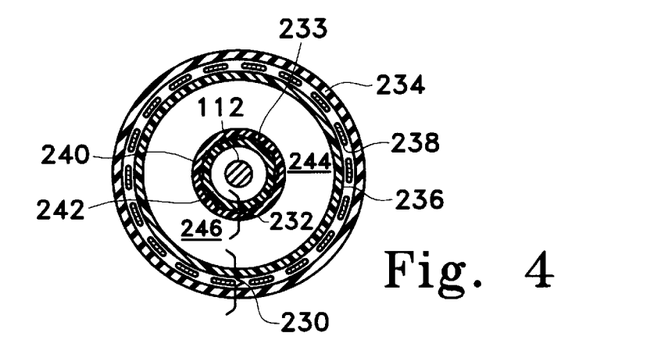
FIG. 4 shows a cross-section along the section lines shown in FIG. 3.

FIGS. 3 and 4 show one highly desirable variation of this invention. These figures show, respectively, in partial cutaway and an end view, the major sections of the catheter assembly which may make up the working shaft of the catheter (102, 104, and 106 in FIG. 1A). In particular, FIG. 3 shows outer tube assembly (230), inner tube assembly (232) and, for purposes of illustration, guidewire (112). These drawings are not to scale so that the various components making up the catheter assembly may be clearly described.

Outer tube assembly (230) is typically made up of three components: exterior covering (234), interior covering (236), and braid (238). Braid (238) may be discontinuous if so desired.

The inner tube assembly (232) typically, although not necessarily, comprises an outer tube covering (240), inner braid (233), and an inner tubing liner (242). Finally, the guidewire (112) is shown within the inner lumen of inner tube assembly (232).

FIG. 4 is a cross-section of the catheter section shown in FIG. 3 and the depicts a central concept of this invention. In particular may be seen the annular space (244) situated between outer tube assembly (230) and inner tube assembly (232). The outer diameter of inner tube assembly (232) is sized in such a way that there is small amount of clearance for flow of inflation fluid between that inner tube assembly (232) outer diameter and the inner surface of outer tube assembly (230). The annular space (244) is hydraulically isolated from the inner lumen of the catheter (236). The inner tubing tube assembly (232) may be considered as spaced from the inner diameter of outer tube assembly (230). Although in some variations one might find such a concept desirable, it is normal in the inventive variation discussed herein, that physical spacers not be placed within the annular space (244). Such spacers would likely inhibit the flow of fluid from the exterior of the catheter to the inflatable membrane and deleteriously affect the flexibility of the catheter by adding small points of significantly higher stiffness. Although we consider the inner tubing assembly (232) to be generally "spaced from" the inner lumen of the outer tubing assembly (230), it should be apparent that since the two are generally affixed to each other only at the very distal tip of the catheter or just proximally of the balloon, and at the most proximal portion of the catheter assembly (100), that there is potential for side-to-side or radial movement of the inner tubing assembly (232) within annular space (244) to the point where it contacts the inner wall of outer tube assembly (230). This, of course, causes "annular" space (244) not to be annular at the point of contact and the region surrounding it, but for the purposes of this invention we will consider that region to be annular for purposes of this invention.

Another major facet of this portion of the invention is the presence of braid (238) as a component of the outer tube assembly (230). The presence of this braid (238) within the outer tube assembly (230) has a surprising array of benefits. Because the individual strands making up braid (238) may be composed of polymeric fibrous strands (e.g., polyesters such as polyethylene terephthalate such as Dacron, polyamides such as the Nylons, LCP's, etc.) or of stainless steels or of a super-elastic alloy such as one containing nickel and titanium, e.g., nitinol, and are ribbon-like, rather than wire-like, the outer tubing assembly (230) provides kink resistance, both to the outer tube assembly (230) and to the inner tube assembly (232) as well. Because the outer tube is kink resistant and yet has significantly large amount of flexibility, vascular catheters made for neurological services in the sizes described below, allow passage of liquid infusate through the lumen of the inner tube member (232) into regions of the body not easily reached before. Additionally, because the inflatable membrane can be used as a temporary occlusion device to block flowing blood through vascular lumen, the placement of a specific drug is much more precise and the concentration of the drug at that delivery site is enhanced. This braid allows the distal tip of the catheter to be stabilized during high pressure infusion of fluids through the innermost lumen and allows for infusion of viscous liquids or liquids containing high amounts of solids or particulates. The presence of the ribbon braid (238) in the outer tubing assembly (230) allows for temporary occlusion of a very distal vascular segments for physiological testing as well as for improved delivery of various treatment agents. Finally, the concentric lumen design has been shown to provide for quick inflation/deflation response. The balloon diameter is also easily controlled with increasing and decreasing pressure.

We have also noted that the outer tubing assembly (230) need not contain braiding (238) along its entire length. The braid (238) should extend for at least about 25% of the distance from the proximal end of the inflatable membrane to the proximal end.

We have found that in some instances, introduction of fluids under pressure into the inner lumen (246) can, in the absence of braid member (233), cause expansion of the walls of the inner tubing assembly (232) and thereby decrease the volume available in the annular space (246) between the outer tubing assembly (230) and inner tubing assembly (232). This expansion causes the balloon to inflate at an inappropraite time. Consequently, we have introduced a braid member (233) in the inner tubing assembly (232) at least for the length typically found within the guide catheter to allay this problem.

Referring again to FIGS. 2 and 3, the materials of construction are as follows: For outer tube assembly (230), the outer covering (234) desirably comprises a polyurethane. Polyurethane is desirable because it is easily placed onto to the outside of the braiding by the laminating techniques described below. It is desirable when producing a catheter such as that shown in FIG. 1A having sections of multiple flexibility to use polyurethanes having different moduli of flexibility and hardness (e.g., durometer values). For instance, in the three flexibility variation of a catheter assembly (100) shown in FIG. 1A, outer covering (234) may be a polymer of another family, e.g., polyolefins such as polyethylene (LLDPE and LDPE), polypropylene, with and without alloying of materials such as polyvinyl acetate or ethylvinyl acetate; polyesters such as various of the Nylons, polyethyleneterephthalate (PET); polyvinylchloride; polysulphones, including polyethersulphones, polyphenyl-sulphones; various ketone-based resins such as polyaryletheretherketone (PEEK) and variations of such as PEKK, PEKEKK; and the like. These are suitable because they may be placed upon the outer surface of the braid (238). Stiffer materials might be placed in the region proximal on catheter assembly (100) shown in FIG. 1A. More flexible materials might be placed on the exterior of section 104 in FIG. 1A and the most flexible on distal region 106 of FIG. 1A. By varying the composition of the materials in this way, a catheter having fairly consistent outside diameter can be produced and yet have the desire flexibility. Again, the most preferred polymeric material used on the outer surface (234) of outer tube assembly (230) is polyurethane. Suitable polyurethanes include such commercially available products as Pellethane (Dow Chemicals) and Carbothane (Thermedics).

Braid (238) is preferably made of a number of polymeric, multi-thread ribbons. The polymer may be selected from known materials such as polyesters (e.g., PET such as Dacron), liquid crystal polymers ("LCP"), polyamides (e.g., Nylons), polyolefins (e.g., polypropylene), Polyaramids (e.g., Kevlar), etc. Braid (238) may also be of a stainless steel or of a super-elastic alloy as discussed elsewhere. Dacron is preferred.

Braid (233) is preferably made of a number of metallic ribbons. Of special desirability are the super-elastic alloys containing nickel and titanium. Of particular significance are the materials known generically as nitinol. These alloys were discovered by the U.S. Naval Ordnance Laboratory. These materials are discussed at length in U.S. Pat. No. 3,174,851 to Bueller et al., U.S. Pat. No. 3,351,463 to Rosner, et al., and U.S. Pat. No. 3,753,700 to Harris, et al. It is common that commercial alloys contain some amount of a member selected from the iron group, e.g., Fe, Cr, Co, etc. These are suitable for use in the class of super-elastic alloys contemplated by this invention. Indeed, it is highly desirable that alloys of the nitinol group contain a modest amount of chromium (up to about 5%). This small amount of iron-group-containing metal in the super-elastic alloys allows superior shape retention after heat treatment. It is our practice to weave the braid shown in the figures on a stainless steel mandrel and, with the braid still on the mandrel, subject the combination to a heating step of a 600 to 700° C. for a few minutes. This heat treatment causes the braid shape to stabilize, but yet the alloy making up the braid retains its super elasticity.

The ribbons making up the braids (233 and 238) are desirably between 0.25 mil and 3.5 mil in thickness and 2.5 mil and 12.0 mil in width. By the term "ribbon," we intend to include elongated shapes, the cross-section of which are not square or round and may typically be rectangular, oval, or semi-oval. They should have an aspect ratio (thickness/ width) of at least 0.5. For super-elastic alloys, including nitinol and those variations containing some amount of iron group metals, the thickness and width may be towards the lower end of those ranges, e.g., down to 0.25 mil and 1.0 mil respectively. Currently available and desirable ribbons include sizes of 0.5 mil by 3 mil, 0.75 mil by 4 mil, 2 mil by 6 mil, and 2 mil by 8 mil.

It is most desirable that a majority of the ribbons making up braid (233) be of a super-elastic alloy. A minor part (less than 35 percent) of the ribbons may be made of ancillary materials. Fibrous materials such as synthetic and natural fibers, e.g., performance polymers such as polyaramid or carbon fibers may be used. In certain applications, more malleable metals and alloys, e.g., gold, platinum, palladium, rhodium, may be used. In those instances, the highly preferred alloy is platinum with a few percent of tungsten. The braids used in this invention may be made using commercially available tubular braiders. By the term "braid," we mean tubular constructions in which the ribbons making up the construction are woven in an in and out fashion so they cross to form a tubular lumen defining a single lumen. The braids may be made up of a suitable number of ribbons, typically six or more. Ease of production on a commercial braider typically results in braids having eight or sixteen ribbons.

The braids (233 and 238) shown in FIG. 3 have a nominal pitch angle with the axis of the braid of 45°. Because the braids have components running both clockwise and counterclockwise around the tubular braids (233 and 238), the angle between the two components is nominally shown as 90°. It is desired for catheters of the type described here that the braid angle to the catheter axis be 45° or less. In those instances where either the diameter of the catheter is varied as a function of the catheter axis (or one wishes to change the stiffness of the catheter in a fashion other than by changing the composition of the polymeric layers adjacent to the braid (233 or 238), it is possible simply to change the pitch angle to another angle.

The inner covering (236) found about tube assembly tube (230) is preferably a lubricious material such as polytetrafluorethylene or other appropriate fluorocarbon polymers, other lubricious polymers such as polyarylenes, and the like. Further, inner liner (236) may be a laminate of polyfluorocarbon on the interior and a polyurethane adjacent to the braid.

The polyurethane and TFE combination is highly desirable, in that the outer surface of the TFE tubing employed may be chemically etched using solutions such as mixtures of metallic sodium and ammonia so that the TFE tubing will form a strong mechanical bond with adjacent polyurethane. When using the methodology described below, the preferred polyurethane is melted into place using a temporary shrink wrap tubing as a forming member. The polyurethane flows through the interstices of the braid and bonds either to the etched polyfluorocarbon surface or to the polyurethane found on the other surface of the braid.

Inner tube assembly (232) is preferably a composite of an outer tubing (240) of polyurethane or other acceptable polymer such as the members found in the list mentioned above, a braid (233) of the materials discussed elsewhere, and an inner tubing (242) of a lubricious material such as TFE. We have found that in certain instances, the polyurethane layer may be omitted, as is shown in further variations of the invention described below.

Finally, the interior of sections shown in FIGS. 3 and 4 may be found in the guide wire. A suitable guidewire for this service is described in U.S. Pat. No. 4,884,579 to Engelson. As was stated above, the particular physical configuration of guidewire forms no critical part of the invention, although it should be quite clear that the catheter assembly described herein is for the specific purpose of following or tracking a guidewire through tortuous vasculature.

Typical ranges of sizes for the portions of the invention shown in FIGS. 3 and 4 and below may be:

TABLE 1

Typical Dimensions (in inches)

| Outer Tubing Assembly (230) | |
| --- | --- |
| Outer Diameter | 0.025 to 0.050 |
| Inner Diameter | 0.020 to 0.045 |
| External Covering (234) | |
| Wall Thickness | 0.001 to 0.004 |
| Internal Covering (236) | |
| Wall Thickness | 0.0005 to 0.003 |
| Annular Space (244) | |
| Outer Diameter | 0.020 to 0.045 |
| Inner Diameter | 0.016 to 0.040 |
| Inner Tubing Assembly (232) | |
| Outer Diameter | 0.016 to 0.040 |
| Inner Diameter | 0.010 to 0.035 |
| External Covering (240) Wall thickness | 0.0005 to 0.003 |
| Inner Covering (242) Wall thickness | 0.0005 to 0.003 |

These dimensions are provided only as guidelines and to assist the reader in understanding the small catheters which are permitted and accomplished as a result of this invention.

Figure 5:
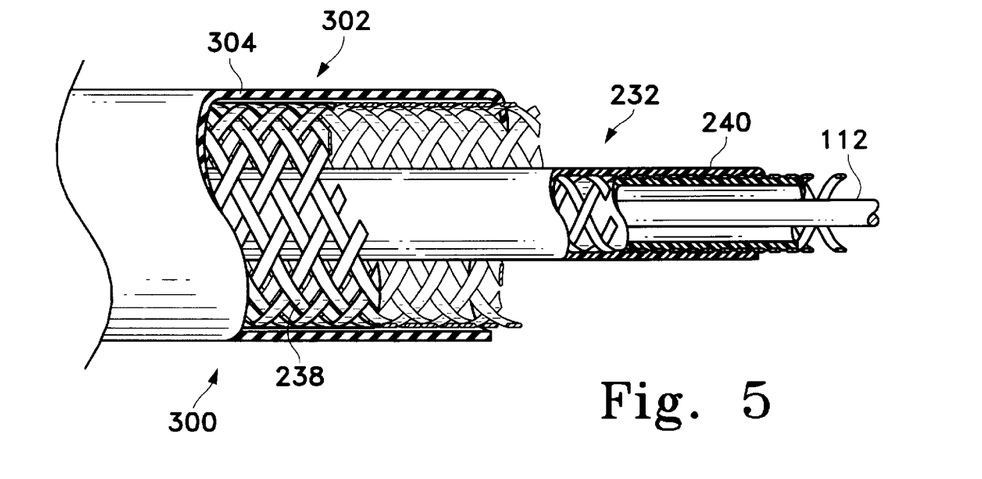
FIG. 5 shows another partial cutaway of another variation of the invention.

FIG. 5 shows another variation of the working shaft of the inventive catheter. In this variation, catheter sector (300) is built similarly to sector (230) found in FIGS. 3 and 4. However, the outer tube assembly (302) comprises only an outer tubing covering (304) and braid (238). Inner tube assembly (232) is made up in the same way as is the inner tubing assembly of FIG. 3. Guidewire (112) remains in the center. Other than the variations noted, the overall structure of assembly (300) is the same as that shown in FIGS. 3 and 4. The composition of the outer tube assembly (302) and its exterior covering (304) may be essentially the same as that described in relation to the external covering (234) in FIGS. 3 and 4. The material making up braid (238) is the same in this configuration as in the earlier drawings.

Figure 6:
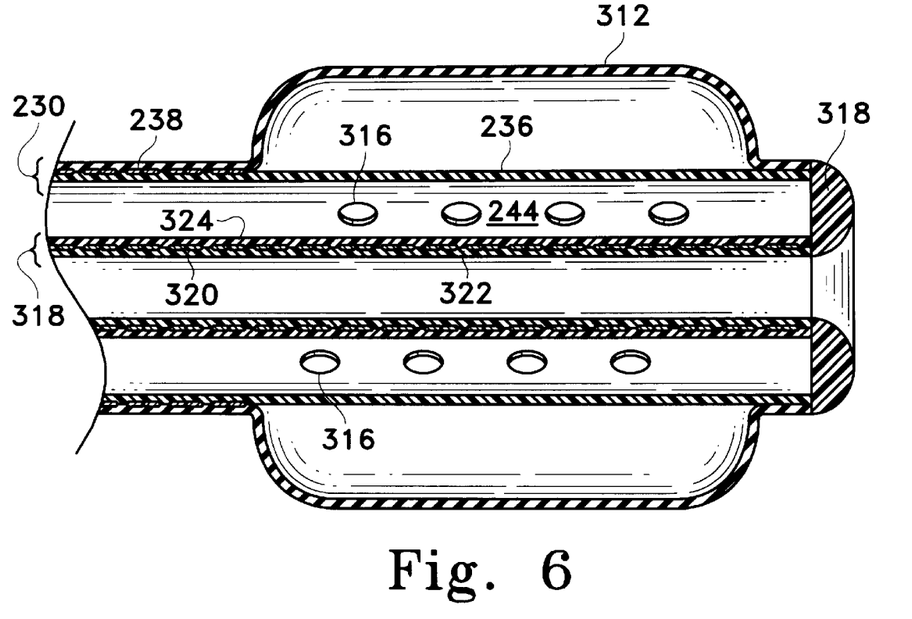
FIGS. 6 and 7 each show different variations of the inflatable balloon in cutaway.

FIG. 6 shows a variation of the inventive device in which a braid (238) is placed in the interface between interior tubing (322) and outer tubing (324). The braid (320) in the interior assembly (318) axially overlaps the braid (318) found in outer tube assembly (230) by an inch or two for most catheters made according to this invention. In this way, the balloon section is provided with a level of stiffness allowing the expandable membrane region to remain sufficiently stiff to follow the guidewire and yet provide a good level of transition from the stiffer, more proximal regions to the more flexible balloon section. As may be determined from these comments, the braid or coil (320) as found in the variation seen in FIG. 6 is, as installed, more flexible than braid (318) in the outer tube assembly (230) as installed.

In this version, interior covering (236) extends into the region of the expandable membrane (312) all the way to the distal tip (318). Again, a number of orifices (316) are desirable to allow fluids to flow from the annular space (244) into the inflatable membrane (312).

Figure 7:
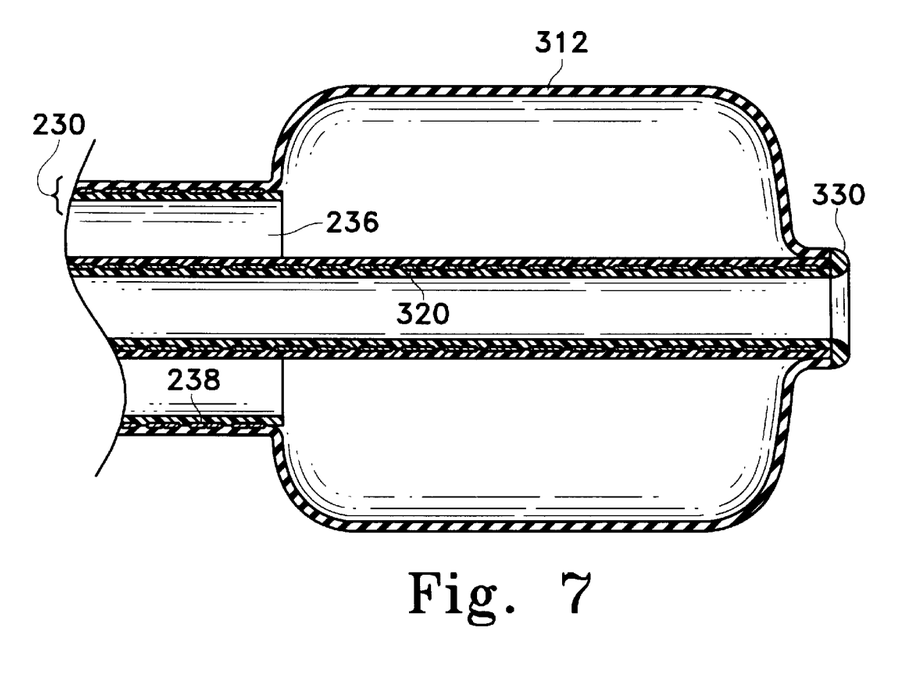

FIG. 7 shows still another variation of this invention, in which the interior covering (236) of outer tube assembly (230) stops distally of expandable membrane (312). This is a simple variation of the embodiment shown in FIG. 6. Braid (320) is again extended all the way to the distal end (330) of the catheter assembly. Because interior covering (236) of outer tube (230) was truncated proximally of expandable membrane (312), the outside diameter of the distal tip (330) may be much smaller. Otherwise, the variation shown in FIG. 7 is quite similar to that shown in FIG. 6. Again, the braid (320) should overlap the super-elastic alloy braid (238) for at least an inch or so to provide sufficient strength, transition, and overall pushability to the catheter assembly.

Figure 8:
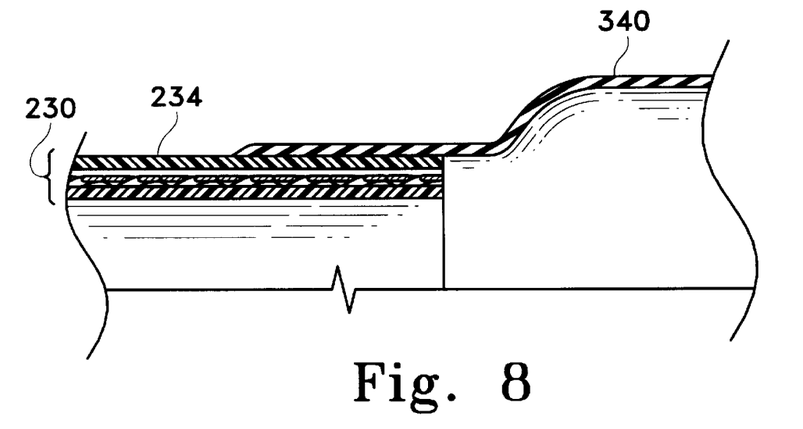
FIG. 8 shows in partial cutaway a variation in which the balloon is attached to an outer section of the outer tubing assembly.
Figure 9:
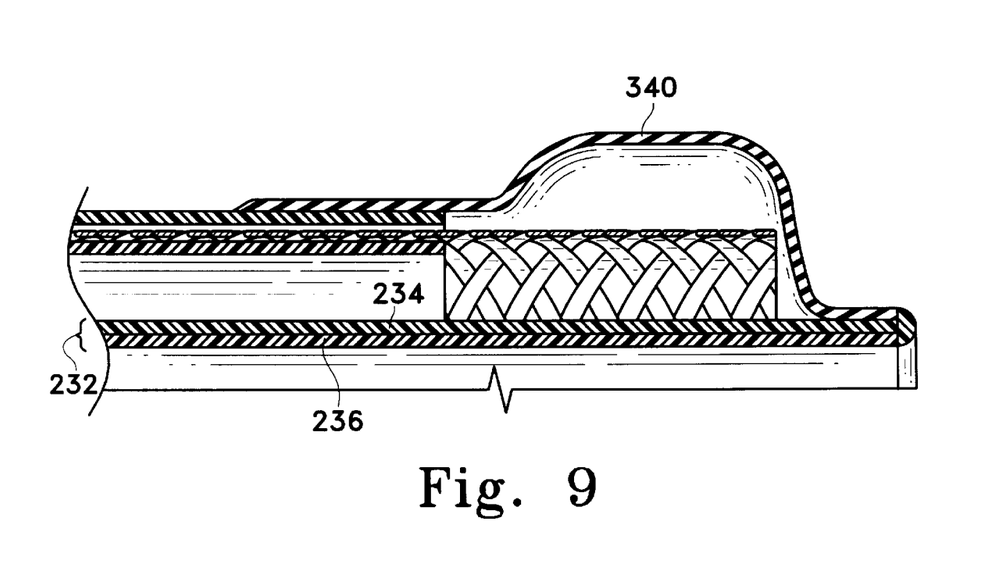
FIG. 9 shows in partial cutaway another variation of the invention in which the braid traverses the opening beneath the inflatable membrane and the balloon joins the inner tubing assembly with a narrow nose.

Each of FIGS. 6 and 7 show the material making up the expandable membrane (312) to butt up against the exterior covering (234) of outer assembly (230). A preferred variation is shown in FIG. 8. In this instance, the tubing making up the expandable membrane (340) is placed exterior to and overlapping for several inches on external covering (234) of outer tubing assembly (230). This provides a more secure seal between the inflatable membrane (340) and the outer tube assembly. Similarly, FIG. 9 shows a variation incorporating the proximal overlap features of expandable membrane (340) and in which the distal end of the expandable membrane (340) is joined to the internal covering (236) and the external covering (234) of inner tube assembly (232). This variation permits the distal tip to be somewhat smaller than most of the variations discussed hereto. Nevertheless, the central lumen remains open for passage of a guidewire infusants.

Figure 10:
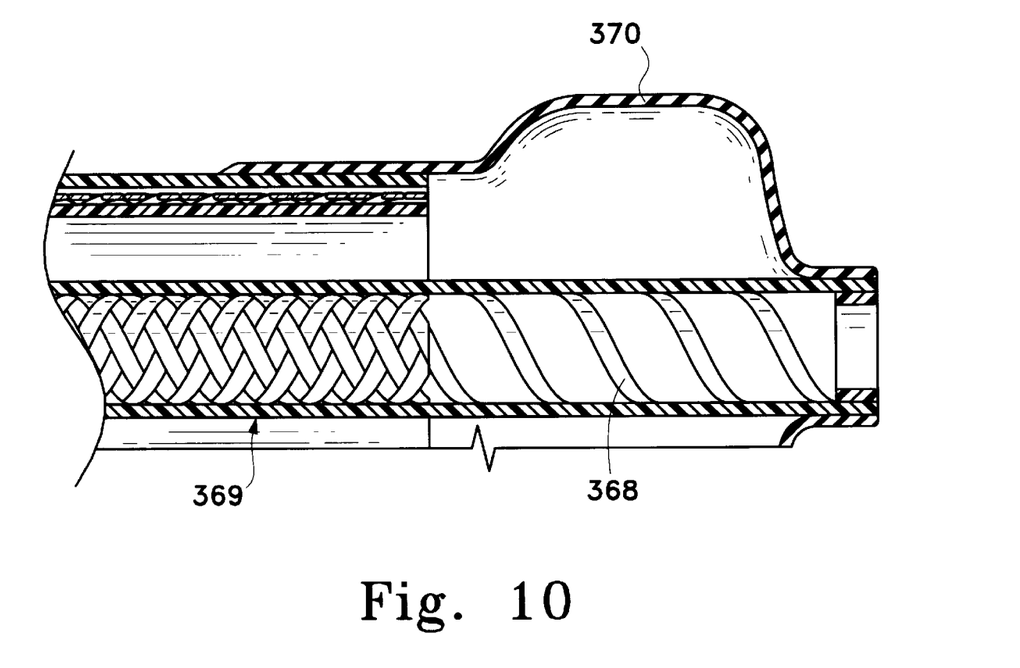
FIG. 10 shows in partial cutaway another variation of the invention in which a coil traverses the opening beneath the inflatable membrane

FIG. 10 shows a variation of the inventive device entailing a coil member (368) in the region of the inner tubing assembly (369) overlapping the distal and proximal regions of the inflatable membrane (370). The remainder of the inner and outer assemblies are as discussed elsewhere herein. The coil (368) is especially useful in small French catheters to provide an added measure of flexibility to the distal end of the overall catheter assembly and yet still provide kink-resistance when using soft, compliant balloons or membranes. The coil member (368) is desirably a metallic ribbon of one of the materials discussed elsewhere, but preferably is a superelastic alloy.

Figure 11A:
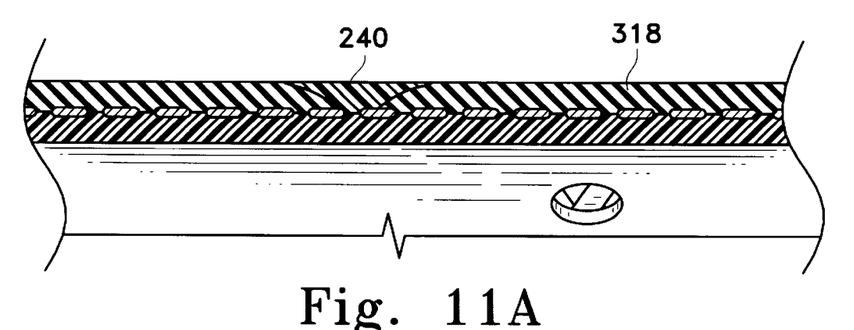
FIGS. 11A, 11B, and 11C show a partial cutaway of a variation of the inflatable membrane utilizing an inflatable marker band to show when the balloon has been adequately inflated.
Figure 11B:
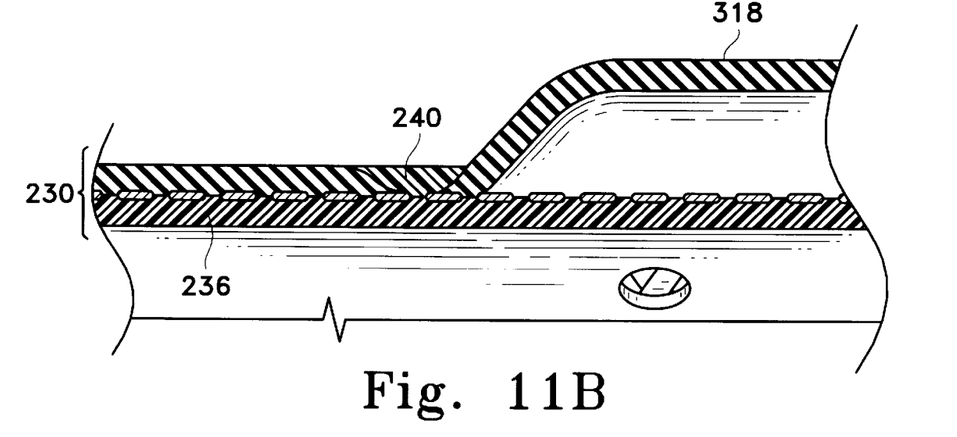
Figure 11C:
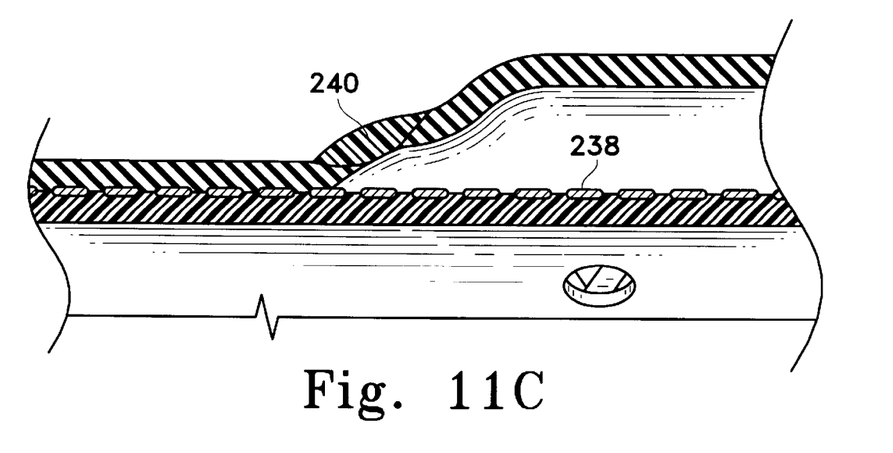

FIGS. 11A, 11B, and 11C show the concept and use of an elastomeric band (240) cast into the proximal region of the expandable membrane (318) in such a way as to serve as an indicator of adequate inflation of the device.

Figure 13A:
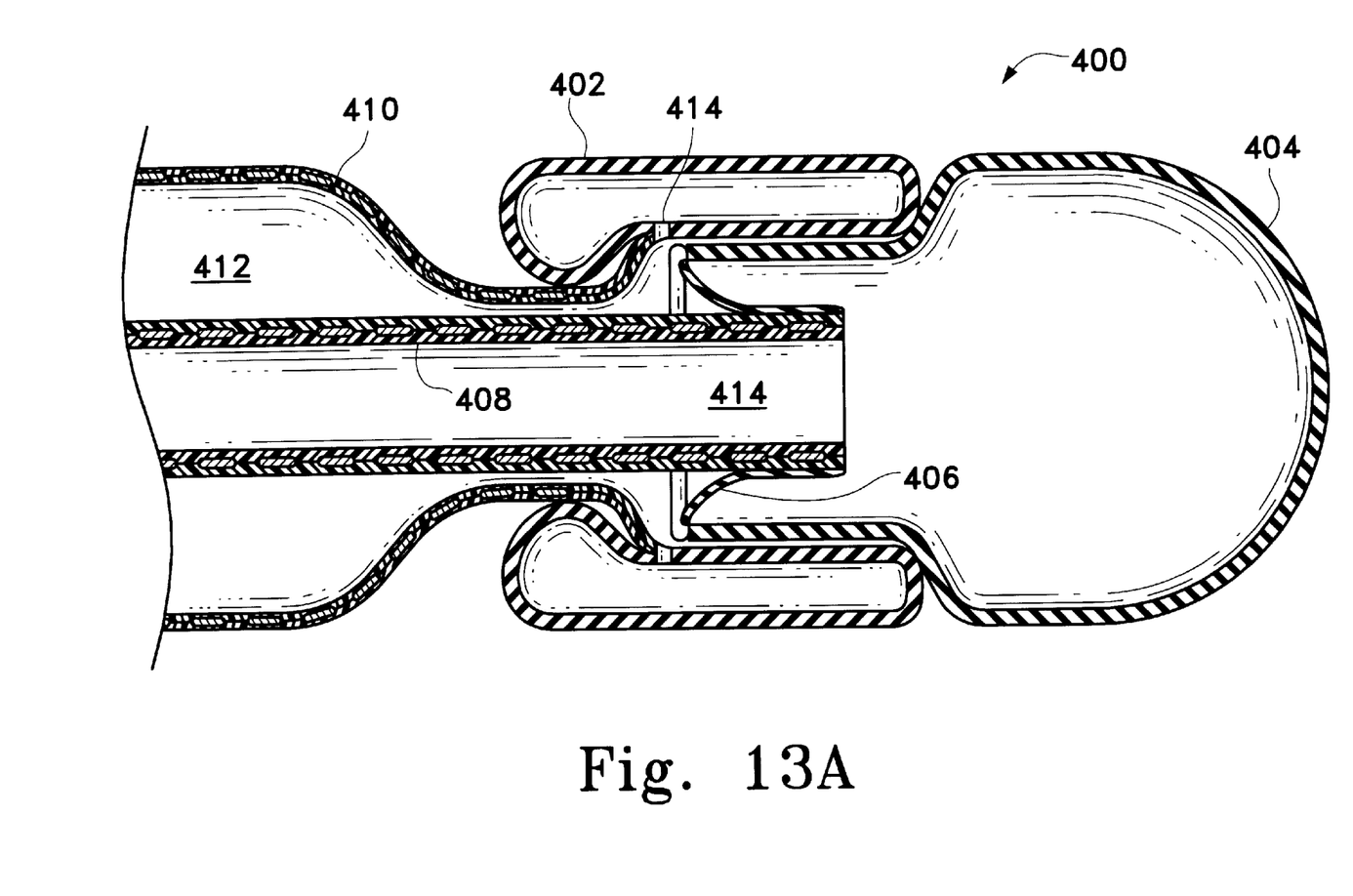
FIGS. 13A, 13B, and 13C show partial, cutaway, side views of a distal tip of the inventive catheter assembly depicting an everting inflatable membrane and a releasable balloon.

FIG. 11A shows an uninflated inflatable membrane (318) bound on its proximal end by a band of warning strip material (340) which is both of a higher durometer rating than the material found in expandable membrane (318) and significantly more radio-opaque. Radio-opacity in such material is provided by a variety of methods. In particular, band (340) may be filled with a radio-opaque filler material such as barium sulphate, bismuth trioxide, bismuth carbonate, powdered tungsten, powdered tantalum, or the like so that it will show up in some contrast to the materials which neighbor it. As an aside, it is within the scope of this invention to include such radio-opaque materials in any of the polymers found herein. It is almost always desirable to be able to see, at least in a slight fashion, the outline of the catheter being introduced into the various regions of the body. It is to be appreciated that most of the tubing utilized in the devices of this invention is of such small size that fluoroscopy is unable to provide a good outline of those devices. There simply is not enough radio-opaque material present. If the region of the body is somewhat dense to fluoroscopy, the invention shown in FIGS. 13A through 13C is nevertheless quite valuable in that it provides a proximal shape to the balloon which indicates that the inflatable membrane is adequately inflated or is near overinflation.

As may be seen in FIG. 11B, at normal inflation, the inflatable membrane (318) rests snugly along the interior covering (236) of outer tube assembly (230). When the radio-opaque band (240) lifts from braid (238) and provides a balloon having a profile as is generally shown in FIG. 11B, it should be apparent to the physician using the device that the inflated membrane is nearing its design limit. Either a new catheter having a larger diameter inflatable membrane (318) should be used if a larger diameter is needed, or the inflatable membrane (318) inflation should be slightly reduced if such is acceptable.

Figure 12A:
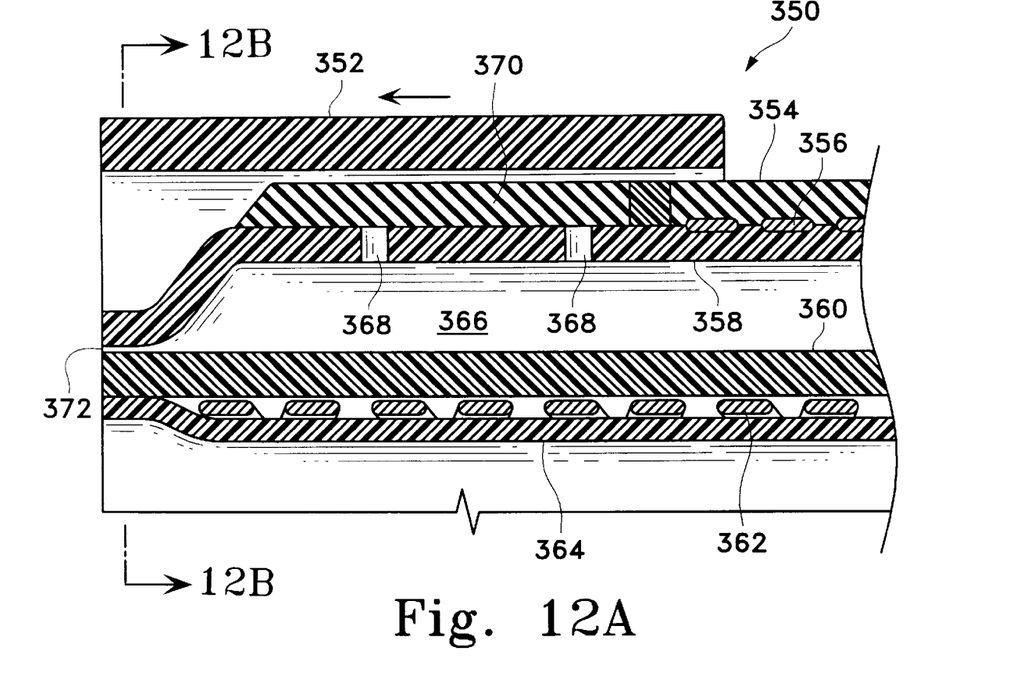
FIGS. 12A and 12B show partial, cutaway, side view and end views of a distal tip of the inventive catheter assembly depicting a bleed port for removing gases from the inventive catheter.
Figure 12B:
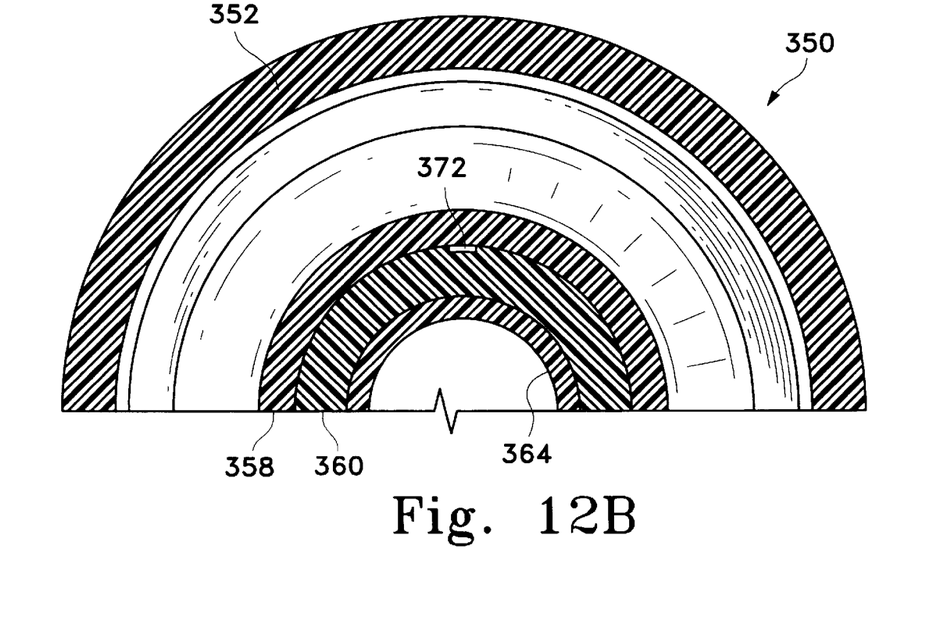

FIGS. 12A and 12B show respectively a partial cutaway side view and a partial cutaway end view of a distal tip of a catheter made according to this invention. In particular, it shows a highly desirable structure and, by the extension, a method for removing air from the annular region of the inventive catheter.

FIG. 12A shows a distal end of a catheter assembly (350) having a purging sheath or constraint sheath (352) an outer tubing assembly made up of an outer polymeric covering (354), a braid member (356) and an inner polymer layer (358). The catheter assembly (350) also has an inner tubing assembly made up of an outer polymer layer (360) a braid member (362) and an inner lubricious polymer layer (364). As is the case with each of the devices described above, the inner tubing assembly and outer tubing assembly are separated from each other so as to form an annular region (366) between the two tubing assemblies. In this variation, a number of orifices (368) pass from the annular region (366) and are used to inflate the inflatable membrane (370).

Central to this variation of the invention is the presence of a small bleed port (372) which passes distally from the annular region (366). This port is sized in such a way that when inflatable membrane (370) is in fact inflated by a passage of fluids from annular region (366) through the fill ports (368), the expansion of the balloon will close the bleed port or ports (372). Only one bleed port (372) is shown in FIGS. 12A and 12B, however this invention contemplates the use of more than one such opening. Bleed constraint sheath (352) is shown in place on the outside of the catheter assembly (350). During the time that this constraint (352) is in place, the bleed ports (372) are open. This allows the person filling the annular region (366) with a liquid to express all of the air found in the annular region (366) before the catheter is placed into a patient. Once the air has been removed via bleed ports (372), the constraining sheath (352) may be removed. The catheter then may be placed in a guide catheter or introducer so to direct the catheter to the desired site.

Otherwise, the catheter assembly (350) shown in FIGS. 12A and 12B share the same advantages and structure as those discussed elsewhere herein.

Figure 13B:
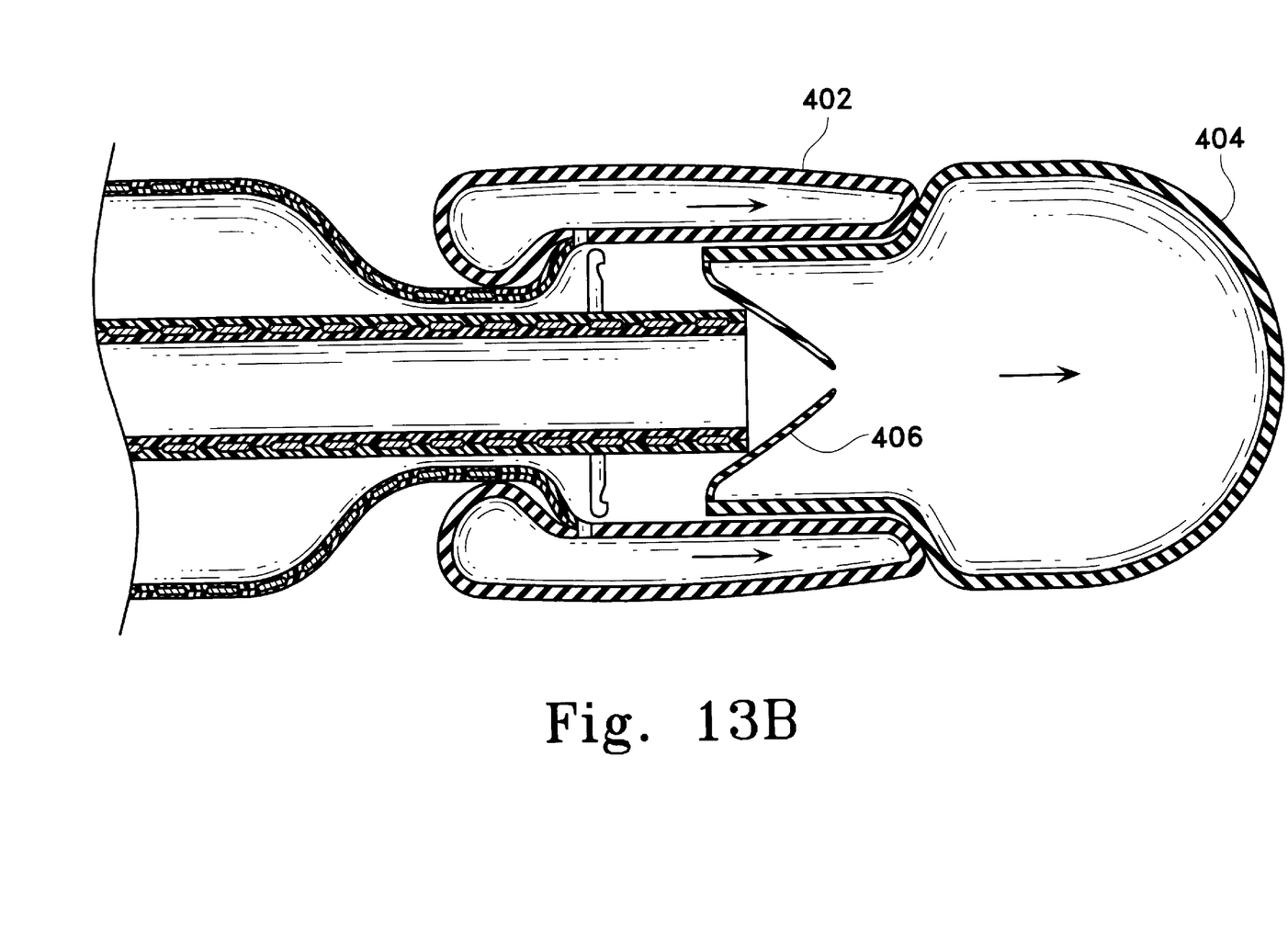
Figure 13C:
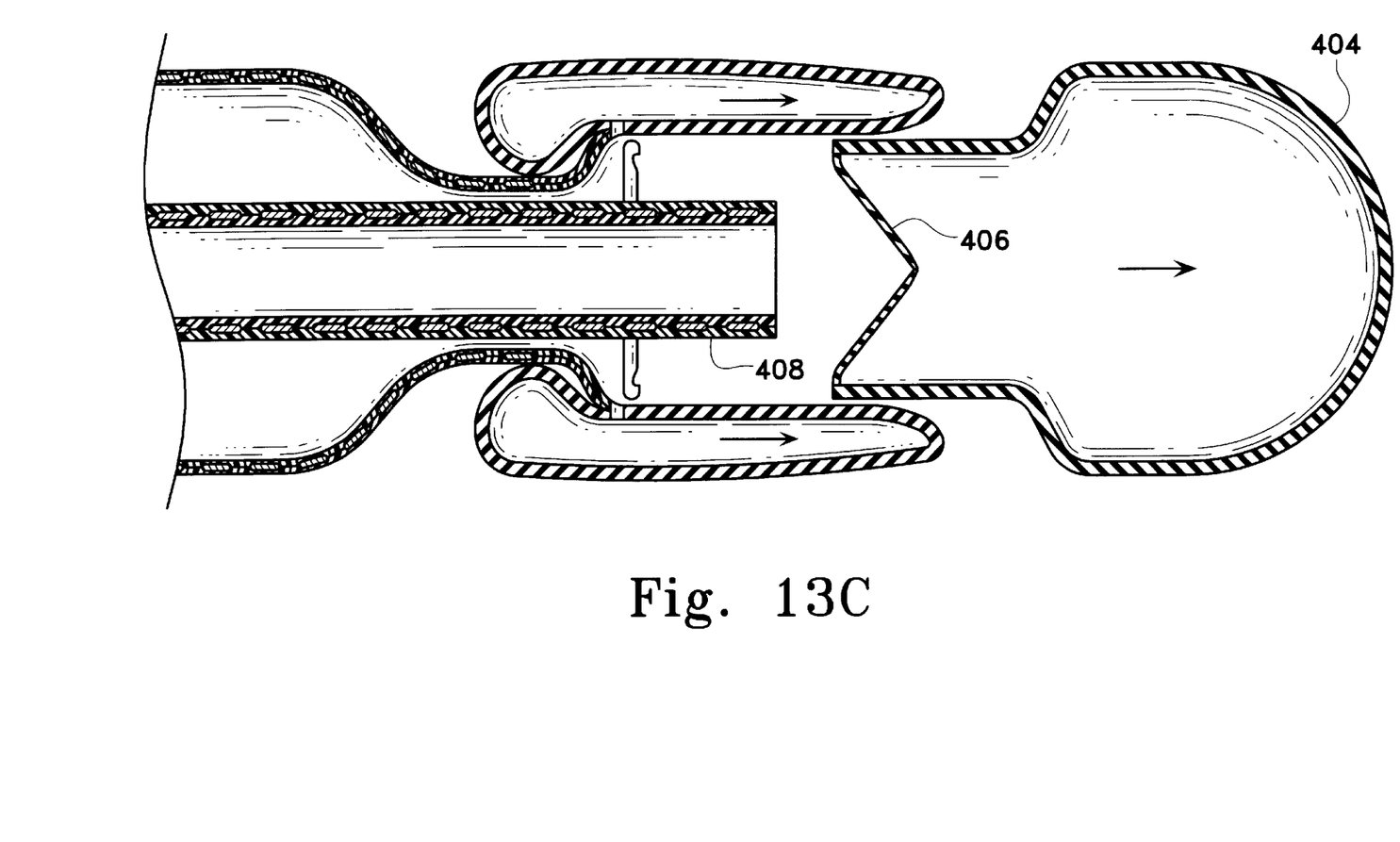

FIGS. 13A, 13B, and 13C show still another variation of the inventive catheter (400). In this variation, the inflatable membrane rather than just expanding outwardly from the axis of the catheter assembly (400) extends distally as well. The specific variation is shown in FIGS. 13A through 13C is an everting balloon (402). In addition to the depiction of the everting balloon (402), the variation shown in FIGS. 13A to 13C provides for a detachable balloon having a self sealing valve (406).

FIG. 13A shows a detachable balloon (404) as seated on catheter assembly (400). Catheter assembly (400) includes an inner tubing assembly (408) and an outer tubing assembly (410) much in the same way that versions discussed above have such variations. The annular region (412) is open to the interior of balloon (402) via one or more small passageways such as (414). The variation shown in FIGS. 12A through 12C show a variation in which the detachable balloon (404) may be inflated through central lumen (414) after introduction of the assembly (400) into the human body. Inflation of detachable balloon 404 may be carried out independently of the inflation of the catheter balloon (402). Evertable balloon (402) is present on the catheter for the express purpose of deploying detachable balloon (400).

Deployment takes place in the following fashion. After the volume interior of detachable balloon (404) is filled via lumen (414), the fluid is introduced through annular region (414) and into the inner space of balloon (402). As is shown in FIG. 13B, balloon (402) begins to expand distally pushing detachable balloon (404) from the distal end of the catheter. The duckbill self-closing valve (406) is shown nearly closed in FIG. 13B.

FIG. 13C shows the balloon clear of the distal end of inner tubing assembly (408) and with the self-closing valve completely closed. Self closing valve (406) is shown to be a duckbill type but other variations of such a valve may be chosen as well. For instance, a valve much like is found in the heart would work equally as well were it to be configured so that it closed upon removal of the tubing assembly from its interior.

Detachable balloons are suitable for a wide variety of uses. They may be used in the place of embolic coils or other variations of embolic materials such as cyanoacrylate glues, glass or polyester beads or fibers, and alike. Detachable balloon (404) may be made of a wide variety of materials which exhibit similarly wide characteristics. For instance, the use of silicone or other expandable compliant balloon materials allows the user of the catheter assembly to make some size choices for the balloon even after the balloon is introduced into the human body. Use of balloons made of non expandable materials, e.g., polyethylene, sets the size of the balloon prior to its entrance into the human body. Choosing a specific size is often highly desirable when using the balloons in fragile blood vessels.

Modification of the above-described variations of carrying out the invention that would be apparent to those of skill in the fields of medical device design generally, and of catheter devices specifically, are intended to be within the scope of the following claims.

We claim as our invention:

1. A catheter assembly for the infusion of fluids comprising outer tubing assembly, an inner tubing assembly, and a membrane assembly:

a) said outer tubing assembly having a proximal end and a distal end and an axis extending from said proximal end to said distal end, said outer tubing assembly comprising an outer polymeric covering extending from said proximal end to said distal end, and a ribbon braid having a plurality of interwoven members disposed interiorly to an interior surface of said outer polymeric covering for at least a portion of said axis, and b) said inner tubing assembly having a proximal end and a distal end and having a lumen extending from said inner tubing assembly proximal end to said distal end, said inner tubing assembly comprising an outer polymeric covering extending from said proximal end to said distal end, and a super-elastic alloy ribbon braid having a plurality of interwoven members disposed interiorly to an interior surface of said outer polymeric covering for at least a portion of said axis, said inner tubing assembly being located within and spaced apart from said outer tubing assembly to form an annular space between said outer tubing assembly and said inner tubing assembly, c) said membrane assembly having a proximal end and a distal end and an outwardly expandable membrane provided on the outer tubing assembly to form an expandable cavity in fluid communication with the annular space between the outer tubing assembly and the inner tubing assembly, and d) further comprising at least one bleed port at a distal end of said annular space between said outer tubing assembly and said inner tubing assembly and said at least one bleed port being sealable by expansion of said expandable membrane.

2. The catheter assembly of claim 1 wherein the outer tubing assembly further comprises an inner polymeric tubing member disposed interiorly to an interior surface of the ribbon braid interwoven members.

3. The catheter assembly of claim 2 wherein the inner polymeric tubing member of the outer tubing assembly comprises a lubricious polymer.

4. The catheter assembly of claim 3 wherein the inner polymeric tubing member of the outer tubing assembly comprises a polyfluorocarbon.

5. The catheter assembly of claim 1 wherein the inner tubing assembly further comprises a lubricious inner polymeric tubing member disposed interiorly to an interior surface of said braid interwoven members.

6. The catheter assembly of claim 5 wherein said superelastic alloy braid interwoven members extend proximally from the distal end of the membrane assembly to a point proximal of the membrane assembly.

7. The catheter assembly of claim 1 wherein the superelastic alloy ribbon braid members extend past the distal end of the outer tubing assembly to the distal end of the inner polymeric tubing assembly.

8. The catheter assembly of claim 1 wherein the outer tubing assembly further comprises an inner polymeric tubing member disposed interiorly to an interior surface of the ribbon braid interwoven members of the outer tubing assembly and the inner polymeric tubing member of the outer tubing assembly extend past a distal end of the outer covering of the outer tubing assembly to the distal end of the inner polymeric tubing assembly and wherein the inner polymeric tubing member on the outer tubing assembly has a tubing wall with at least one orifice to allow fluid communication through the tubing wall between the expandable cavity in fluid communication with the annular space between the outer tubing assembly and the inner tubing assembly.

9. The catheter assembly of claim 1 wherein the superelastic alloy ribbon braid interwoven members on the outer tubing assembly terminate at the proximal end of the membrane assembly.

10. The catheter assembly of claim 1 wherein the outer polymeric covering of the outer tubing assembly comprises at least two sections of different stiffness.

11. The catheter assembly of claim 10 wherein the outer polymeric covering of the outer tubing assembly comprises a proximal section of relatively low flexibility, a distal of relatively high flexibility, and a mid section having a flexibility intermediate between that of the proximal and distal sections.

12. The catheter assembly of claim 1 wherein the outer polymeric covering of the outer tubing assembly comprises a polyurethane.

13. The catheter assembly of claim 1 wherein the inner polymeric tubing member of the inner tubing assembly comprises a polyfluorocarbon.

14. The catheter assembly of claim 1 wherein the expandable membrane further expands distally upon inflation.

15. The catheter assembly of claim 1 wherein the outer tubing assembly braid interwoven members comprise polymeric ribbon.

16. The catheter assembly of claim 15 wherein the outer tubing assembly braid interwoven members comprise polyethylene terephthalate ribbon.

17. A catheter assembly for the infusion of fluids comprising an outer tubing assembly, an inner tubing assembly, a membrane assembly, and a releasable balloon:

a) said outer tubing assembly having a proximal end and a distal end and an axis extending from said proximal end to said distal end, said outer tubing assembly comprising an outer polymeric covering extending from said proximal end to said distal end, and a ribbon braid having a plurality of interwoven members disposed interiorly to an interior surface of said outer polymeric covering for at least a portion of said axis, and b) said inner tubing assembly having a proximal end and a distal end and having a lumen extending from said inner tubing assembly proximal end to said distal end, said inner tubing assembly comprising an outer polymeric covering extending from said proximal end to said distal end, and a super-elastic alloy ribbon braid having a plurality of interwoven members disposed interiorly to an interior surface of said outer polymeric covering for at least a portion of said axis, said inner tubing assembly being located within and spaced apart from said outer tubing assembly to form an annular space between said outer tubing assembly and said inner tubing assembly, c) said membrane assembly having a proximal end and a distal end and an outwardly expandable membrane provided on the outer tubing assembly to form an expandable cavity in fluid communication with the annular space between the outer tubing assembly and the inner tubing assembly, and d) said releasable balloon in fluid communication with a distal portion of said lumen and releasably attached to at least one of said outer and inner tubing assemblies distally of said expandable membrane so as to be released upon inflation of said expandable membrane.

18. The catheter assembly of claim 15 wherein said releasable balloon further comprises a one-way valve adapted to accept fluid from said inner tubing assembly lumen.

* * * * *